United States Patent
Siddalingappa

(10) Patent No.: US 11,058,745 B1
(45) Date of Patent: Jul. 13, 2021

(54) STABLE LIQUID PHARMACEUTICAL COMPOSITIONS OF DAPTOMYCIN

(71) Applicant: JNF LLC., Princeton, NJ (US)

(72) Inventor: Basavaraj Siddalingappa, Gujarat (IN)

(73) Assignee: GOOD HEALTH, LLC, Princeton, NJ (US)

( * ) Notice: Subject to any disclaimer, the term of this patent is extended or adjusted under 35 U.S.C. 154(b) by 20 days.

(21) Appl. No.: 16/583,673

(22) Filed: Sep. 26, 2019

Related U.S. Application Data

(60) Provisional application No. 62/741,187, filed on Oct. 4, 2018.

(51) Int. Cl.
| | | |
|---|---|---|
| *A61K 38/12* | (2006.01) | |
| *A61K 47/14* | (2017.01) | |
| *A61K 47/10* | (2017.01) | |
| *A61K 47/18* | (2017.01) | |
| *A61K 9/08* | (2006.01) | |
| *A61K 47/02* | (2006.01) | |

(52) U.S. Cl.
CPC .............. *A61K 38/12* (2013.01); *A61K 9/08* (2013.01); *A61K 47/02* (2013.01); *A61K 47/10* (2013.01); *A61K 47/14* (2013.01); *A61K 47/183* (2013.01)

(58) Field of Classification Search
None
See application file for complete search history.

(56) References Cited

U.S. PATENT DOCUMENTS

| | | | |
|---|---|---|---|
| 8,431,539 | B2 | 4/2013 | Palepu et al. |
| 2002/0111311 | A1 | 8/2002 | Govardhan et al. |
| 2017/0239335 | A1 | 8/2017 | Sonavaria et al. |
| 2017/0348382 | A1* | 12/2017 | Kurade .................. A61K 47/40 |

FOREIGN PATENT DOCUMENTS

| | | |
|---|---|---|
| EP | 0386951 A2 | 9/1990 |
| EP | 3417849 A1 | 12/2018 |
| WO | 2005049061 A2 | 6/2005 |
| WO | 2014041425 A1 | 3/2014 |
| WO | 2016059587 A9 | 4/2016 |
| WO | 2016059592 A1 | 4/2016 |

* cited by examiner

*Primary Examiner* — Kyung S Chang
(74) *Attorney, Agent, or Firm* — Lucas & Mercanti, LLP

(57) ABSTRACT

Daptomycin-containing formulations having extended stability are disclosed. The formulations are substantially non-aqueous liquid compositions containing daptomycin, cysteine, magnesium chloride, and propylene glycol. In alternative embodiments, the formulations include glycerol and optionally auxiliary solvents such as ethanol.

14 Claims, No Drawings

STABLE LIQUID PHARMACEUTICAL COMPOSITIONS OF DAPTOMYCIN

CROSS-REFERENCE TO RELATED APPLICATIONS

This application claims the benefit of priority from U.S. Provisional Application No. 62/741,187 filed Oct. 4, 2018, the contents of which are incorporated herein by reference.

FIELD OF INVENTION

The present invention relates to daptomycin liquid compositions comprising propylene glycol and stabilizers.

BACKGROUND OF THE INVENTION

Protein and peptide therapeutics are increasingly used these days to treat many disease conditions. However, the unstable nature of these molecules makes them difficult formulate into liquid compositions. Hence many peptide drugs are available as powder for reconstitution prior to injection.

Daptomycin is a lipopeptide antibiotic used in the treatment of systemic and life-threatening infections caused by Gram-positive organisms. It is a naturally occurring compound found in the soil, saprotroph *Streptomyces roseosporus*. Its distinct mechanism of action makes it useful in treating infections caused by multiple drug-resistant bacteria. It is indicated for the treatment of adults with *Staphylococcus aureus* bacteremia, including those with right-sided infective endocarditis, caused by methicillin-susceptible and methicillin-resistant isolates. It is also used for the treatment of skin and skin structure infections.

Daptomycin is a cyclic lipopeptide and has good solubility in water and aqueous buffers which makes it amenable for parenteral formulation development. However, it is very unstable in water and aqueous buffers. In mildly acidic conditions, daptomycin degrades by aspartyl transpeptidation at asp-9 residue. This pathway involves the reversible formation of a succinimido intermediate formed by attack of a peptide nitrogen on the carbonyl side chain of asp-9 and subsequent reversible formation of two aspartic acid isomers. Also, ester hydrolysis, asparginyl deamidation, peptide bond cleavage contribute degradation. In alkaline pH, hydrolysis at C-terminus (kynurenine) and the side chain of the fourth residue (threonine) major degradation pathways (Muangsiri, W., & Kirsch, L. E. (2001). The kinetics of the alkaline degradation of daptomycin. Journal of Pharmaceutical Sciences, 90(8), 1066-1075).

The daptomycin injectable formulations were reported in aqueous buffers having pH between 6-8. See, for example U.S. Pat. No. 8,431,539. Although such formulations were reported to be sustainably free from impurities, examples indicated 5-10% impurities.

Similarly, ready to use solutions of daptomycin in non-aqueous solvents are described in PCT publications WO2016/059587 and WO2016/059592. However, inadequate stability for such products is anticipated. As such there are no reported liquid formulations of daptomycin which are very pure and free from impurities compared to the solid drug substance stored at such conditions.

Commercially available parenteral formulations of daptomycin come as lyophilized powder with brand name Cubicin and Cubicin RF. Cubicin which has only daptomycin and sodium hydroxide in the composition, is unstable at room temperature conditions. After reconstitution, the solution is stable for only a few hours. Cubicin RF is a reformulated version of Cubicin and has sucrose in addition to NaOH as excipients. The product is more stable at room temperature conditions due stabilizing effects of sucrose.

The simple way to formulate highly unstable drugs as liquid parenteral formulations is to use non-aqueous pharmaceutically acceptable cosolvents. However, the poor solubility of daptomycin in commonly used solvents such as PEG is great problem in developing liquid formulations. Even small molecular weight PEG's are often used to crystallize daptomycin from solutions. See US 2002/0111311.

Aqueous buffered or un-buffered isotonic solutions of drugs are preferred form of the injections for intravenous route. However, many such products are formulated using cosolvents, solubilizers and stabilizers. Various molecular weight PEG's such as PEG 300, PEG 400, PEG 600 are commonly used solvents for intravenous formulation. Similarly, ethanol and propylene glycol are also used extensively in the intravenous products.

Some drugs degrade rapidly in aqueous or semi-aqueous solutions and are formulated in non-aqueous solvents such as PEG 400, 600 etc. Acids, alkali's, chelating agents, antioxidants and other stabilizing agents are sometimes included in the product to increase shelf life and patient compliance.

SUMMARY OF THE INVENTION

Daptomycin is unstable aqueous buffered and un-buffered solutions. Hence the formulations of the invention are formulated using selected co-solvents and appropriate stabilizers. This invention includes stable liquid formulations of daptomycin in non-aqueous or semi-aqueous solutions with appropriate stabilizers.

In some preferred embodiments, the inventive liquid compositions include from about 25 to about 250 mg/ml of daptomycin; from about 1.0 to 10 mg/ml cysteine; from about 1.0 to about 10 mg/ml of $MgCl_2$. The compositions further include a preferably non-aqueous solvent comprising propylene glycol (PG). The non-aqueous solvent can include a co-solvent which is preferably glycerin amounts of from >0 up to 90% V/V. Further aspects of the invention include solvent mixtures containing 90:10 PG: glycerin or 80:20 PG:glycerin. In other embodiments, the solvent includes a mixture of PG and glycerol wherein the PG makes up at least about 50% of the solvent blend and is preferably at least about 60%. Preferable amounts of glycerol are from about 35% to about 45% with amount of about 40% being more preferred. All percentages for the liquid components of the composition are based on V/V basis. Further aspects of the invention include methods of preparing the daptomycin compositions and methods of treatment using the same.

For purposes of the present invention, "about" shall be understood to mean shall be understood herein to mean less than or equal to a 5-10% deviation from the recited value. For example, a concentration of about 20% (v/v) means a concentration of 20%.+−0.5 or 10%.

For purposes of the present invention, "daptomycin" shall be understood to include all pharmaceutically acceptable forms of daptomycin, including any pharmaceutically acceptable salts thereof, i.e. the HCl, etc.

For purposes of the present invention, "non-aqueous" liquids shall be understood to include liquids which contain negligible amounts of water, i.e. <about 5.0%, preferably <about 2%.

DETAILED DESCRIPTION OF THE INVENTION

This invention relates to stable liquid injectable formulations of daptomycin in pharmaceutically co-solvents and mixtures thereof. In accordance with certain preferred embodiments, the compositions of the invention are stable, liquid daptomycin compositions, comprising
 a. from about 25 to about 250 mg/ml of daptomycin;
 b. from about 1.0 to about 10 mg/ml cysteine;
 c. from about 1.0 to about 10 mg/ml magnesium chloride; and
 d. a solvent comprising propylene glycol, which, in some aspects, is in amounts of from about 10 to about 100% V/V; in further aspects, the solvent optionally further comprises glycerol, in amounts of from about >0 to about 90% V/V.

The daptomycin concentration is preferably about 50 mg/ml or 150 mg/ml.

Some preferred solvent mixtures include those in which the blend of PG and glycerol is about 90:10 and in further aspects, the blend is about 60:40. It will be appreciated and understood by those of ordinary skill that the non-aqueous solvent mixture can include any amounts of PG, glycerin and auxiliary cosolvents within the stated ranges, For example, the PG may present in amounts of 50, 51, 52, 53 etc. up to 100%. Likewise, the amounts of glycerin can be any amount within the range, i.e. 20, 21, 22 . . . etc. up to 90%.

If desired, auxiliary cosolvents can be included therewith such as PEG 300, 400, 600, or ethyl alcohol. The auxiliary cosolvents can be present in amounts of from about >0 up to about 50% V/V of the solvent mixture and amounts of from about 10 to about 40% V/V being used in some embodiments. Moreover, auxiliary excipients useful in the field of pharmaceutical formulations such as a cyclodextrin like hydroxy propyl cyclodextrin can be included. The PG and principal cosolvent glycerin are available from readily recognizable commercial sources and are suitable for use in parenteral formulations.

The inventive compositions include cysteine, however other stabilizers can also be included such as other amino acids or stabilizers know to those of ordinary skill. In addition, the inventive compositions can include an alkali such as meglumine, tromethamine, or sodium hydroxide to attain favorable pH for stability.

If desired, the compositions can also include a second metal salt in addition to the magnesium chloride such as calcium chloride or others well known to those of ordinary skill.

The amount of magnesium chloride present in the compositions in some aspects of the invention is from about 3 to about 10 mg/ml, with amounts of about 4 or about 6 mg/ml being more preferred. The amount of cysteine present in the compositions of the invention in some aspects of the invention is from about 1 to about 3 mg/ml, with amounts of about 2 mg/ml being more preferred. It has been surprisingly found that non-aqueous liquid compositions containing a blend of PG and glycerol as well as cysteine and magnesium chloride have extended stability as compared to formulations of the prior art.

In accordance with the foregoing some preferred liquid, non-aqueous formulations having extended storage stability include:

| Ingredient | Amount - Range |
|---|---|
| Daptomycin | 50-150 mg/ml |
| Cysteine | 1-3 mg/ml |
| MgCl$_2$ | 3-5 mg/ml |
| PG | 50%-90% vol. |
| Glycerol | 10%-40% vol. |

Additional aspects of the invention include formulations wherein concentration of daptomycin is about 50 mg/mi; the concentration of magnesium chloride is about 4 mg/ml and the concentration of cysteine is about 2 mg/ml; and others wherein the formulations include a concentration of daptomycin of about 150 mg/ml; the concentration of magnesium chloride is about 6 mg/ml and the concentration of cysteine is about 2 mg/ml. In each case, the formulations include a solvent mixture containing about 60% PG and about 40% glycerol.

The compositions or formulations of the invention have improved stability and clarity as compared to the formulations of the prior art. For example, the compositions demonstrate substantial optical clarity after 1 month at 25° C./60% relative humidity. The amount of daptomycin impurities in these inventive compositions is preferably about 5% or less under these same conditions. Other formulations demonstrate substantial optical clarity after 2 months at 25° C./60% relative humidity and have amounts of daptomycin impurities of about 9.5% or less. Still further liquid formulations in accordance with the present invention demonstrate substantial stability after 1 year under refrigerated conditions.

For purposes of the present invention, "stable" or "substantially stable" with respect to liquid daptomycin compositions shall be understood to mean compositions having less than about 5% anhydrodaptomycin impurity compared to a reference standard and/or having a peak purity of at least about 95% after 1 month at room temperature or 12 months at refrigerated temperatures of from about 2 to about 8° C. Impurity and peak purity calculated based on integration of major impurity anhydrodaptomycin and daptomycin peaks only and minor impurities not accounted for calculations.

It is also contemplated that the compositions of the present invention will be provided as bulk solutions which can be dispensed as multi-dose vials containing from, for example, about 500 mg to several grams of daptomycin. The vials containing daptomycin are preferably sealed under pharmaceutically acceptable aseptic conditions using sterile fill techniques with vails made of glass or other suitable inert material which are sealed using aluminum or other suitable crimp caps and include rubber stoppers, etc. in accordance with generally acceptable techniques. The vials can be stored under refrigerated conditions and the liquid daptomycin compositions will demonstrate sufficient stability for about a year or longer. Upon need, the appropriate dose of daptomycin is drawn from the bulk container such as via syringe and diluted into an appropriate physiologically acceptable fluid such as normal saline before being administered to a patient in need thereof either by IV injection or infusion in a manner well known to those of ordinary skill.

Thus, further aspects of the invention include methods of treating a daptomycin-responsive condition, comprising administering an effective amount of the daptomycin composition described herein to a patient in need of such treatment. The methods can include administering the compositions to the patient via intravenous injection with or without further dilution or stated alternatively the compositions are administered as an intravenous infusion or as a short time injection after appropriate dilutions with isosmotic fluids. Without limitation, suitable doses can be about 4-8 mg/kg body weight once daily administered at a concentration of about 50 mg/ml of daptomycin.

DETAILED DESCRIPTION OF THE INVENTION

Description of Examples

Example 1: Solubility Testing of Daptomycin in Co-Solvents

TABLE 1

Solubility of Daptomycin in organic solvents

| Daptomycin | Solvent | Observations |
|---|---|---|
| 20 mg | Propylene glycol, 1 mL | Clear after 5 minutes sonication |
| 20 mg | PEG 400, 1 mL | Turbid after 10 minutes sonication |
| 20 mg | PEG 300, 1 mL | Turbid after 10 minutes sonication |
| 20 mg | PEG 200, 1 mL | Turbid after 10 minutes sonication |
| 20 mg | PEG 600, 1 mL | Turbid after 10 minutes sonication |
| 20 mg | Ethanol, 1 mL | Turbid after 10 minutes sonication |

Result: The daptomycin is only soluble in propylene glycol and can be used in the formulation of daptomycin injection.

Example 2: Formulations of Daptomycin with Propylene Glycol, No Cysteine

TABLE 2

Daptomycin formulation 1

| Ingredients | Formulation no 1 |
|---|---|
| Daptomycin | 1000 mg |
| Propylene Glycol | 10 ml |

Process:
Daptomycin was taken in 20 mL vial and propylene glycol was added and sonicated until a clear solution is formed.

TABLE 3

Stability data of Formulation 1:

| | | Formulation no 1 | |
|---|---|---|---|
| Stability time period | Temp/humidity | Peak purity % | Impurity % |
| 1 Month | 2-8° C. | 98.83 | 1.17 |
| | 25 C./60% RH | 77.05 | 22.95 |
| 2 Months | 2-8° C. | 97.44 | 2.56 |
| | 25 C./60% RH | 55.68 | 45.32 |
| 3 months | 2-8° C. | 97.51 | 2.49 |
| 4 months | 2-8° C. | 95.28 | 3.64 |

Note: Impurities presented here represent increase compared to standard injections. The peak at RRT of about 1.12 (Anhydrodaptomycin) is major impurity that increases over the time. The same impurity is also present in standard injections to the extent of 0.6 to 0.8%. Here onwards, impurity means it is Anhydrodaptomycin and peak purity refers to area percentage of Daptomycin, when only two peaks are integrated, Daptomycin and Anhydrodaptomycin.

Results:
With only propylene glycol, daptomycin is stable up to 1 month at 2-8° C. and starts to degrade after 2 months.

Example 3: Formulations with Propylene Glycol and Various Amino Acids

TABLE 4

Daptomycin compositions with amino acids

| | Formulation no | | | | |
|---|---|---|---|---|---|
| Ingredients | 2 | 3 | 4 | 5 | 6 |
| Daptomycin | 10 mg | 10 mg | 10 mg | 10 mg | 10 mg |
| Propylene Glycol | 1 ml | 1 ml | 1 ml | 1 ml | 1 ml |
| Arginine | 10 mg | — | — | — | 2.5 mg |
| Cystine | — | 10 mg | — | — | 2.5 mg |
| Glycine | — | — | 10 mg | — | 2.5 mg |
| Lysine | — | — | — | 10 mg | 2.5 mg |

Process:
Daptomycin and amino acids were taken in 20 mL vial and Propylene glycol was added and sonicated until clear solution was formed. Note: In case of Arginine and Glycine, there was some turbidity.

TABLE 5

Stability data for the formulations 2-6

| | | Formulation no | | | | | | | | |
|---|---|---|---|---|---|---|---|---|---|---|
| | | 2 | | 3 | | 4 | | 5 | | 6 | |
| Stability time period | Temp/ Humidity | Peak purity % | Imp % | Peak purity % | Imp % | Peak purity % | Imp % | Peak purity % | Imp % | Peak purity % | Imp % |
| 1 day | 25 C./60% RH | 99.14 | 0.86 | 98.94 | 1.06 | 98.78 | 1.22 | 98.60 | 1.40 | 98.08 | 1.92 |
| 4 day | 25 C./60% RH | 99.41 | 0.59 | 98.61 | 1.39 | 97.48 | 2.52 | 98.79 | 1.21 | 95.56 | 4.44 |
| 11 day | 25 C./60% RH | 74.96 | 24.16 | 97.63 | 2.37 | 91.99 | 8.01 | 84.16 | 15.84 | 87.13 | 12.87 |

TABLE 5-continued

Stability data for the formulations 2-6

| | | Formulation no | | | | | | | | |
|---|---|---|---|---|---|---|---|---|---|---|
| | | 2 | | 3 | | 4 | | 5 | | 6 |
| Stability time period | Temp/ Humidity | Peak purity % | Imp % | Peak purity % | Imp % | Peak purity % | Imp % | Peak purity % | Imp % | Peak purity % | Imp % |
| 16 day | 25 C./60% RH | — | — | 95.58 | 4.42 | — | — | — | — | — | — |

Results:

Among the amino acids tested, cysteine was found to be better stabilizer compared to other amino acids tested. The formulation containing cysteine was stable up to 11 days with just 2.5% of additional impurity, which was also present in standard injection up to 0.92%. None of the formulations without cysteine were found to be stable to this extent. In many of the cases, impurity rose to 2.5% in just two days.

Example 4: Formulations with Calcium Chloride and Magnesium Chloride

TABLE 6

Formulation composition for Form 7-8

| Ingredients | Formulation 7 | Formulation 8 |
|---|---|---|
| Daptomycin | 250 mg | 250 mg |
| Propylene Glycol | 5 ml | 5 ml |
| Hydroxy propyl-b-cyclodextrin | 100 mg | 100 mg |
| Magnesium Chloride | 0.0 | 25 mg |
| Cystine | 50 mg | 50 mg |
| Calcium Chloride | 25 mg | 0.0 |

Process:

Daptomycin and other excipients were taken in propylene glycol and sonicated until clear solutions were formed.

TABLE 7

Stability data of formulations 7

| Stability time period | Temp/humidity | Peak purity % | Impurity % |
|---|---|---|---|
| Initial | 2-8° C. | 98.99 | 1.01 |
| 1 days | 40 C./75% RH | 99.09 | 0.91 |
| 2 days | 25 C./60% RH | 99.07 | 0.93 |
| 4 days | 40 C./75% RH | 97.97 | 2.03 |
| 12 days | 40 C./75% RH | 94.88 | 5.12 |
| 16 days | 25 C./60% RH | 98.07 | 1.93 |

No analysis done at 2-8° C. after one month as formulation was turbid.

TABLE 8

Stability data of Form 8

| Stability time period | Temp/humidity | Peak purity % | Impurity % |
|---|---|---|---|
| Initial | — | 99.16 | 0.84 |
| 3 days | 40 C./75% RH | 98.26 | 1.74 |
| 10 days | 40 C./75% RH | 95.23 | 4.77 |
| 1 month | 25 C./60% RH | 97.38 | 2.62 |
| 1 month | 2-8 C. | 99.12 | 0.87 |

Result: Form 8, found to be more stable physically and chemically compared to Form 7 though composition is same for both formulation except for in organic salt and hence magnesium chloride was able enhance physical stability of composition with formulation being clear for 1.5 months at 2-8° C.

Other excipient Hydroxy Propyl-β-Cyclodextrin has no significant effect on stability.

TABLE 9

Physical Stability data of Form 7 and 8

| Parameter | Form 7 (Formulation with Calcium chloride) | Form 8 (Formulation with Magnesium chloride) |
|---|---|---|
| Physical clarity | Clear for about 4 days at 40° C./75% RH and about 6-8 days 25° C./60% RH Turns turbid after about 15 days when stored at 2-8° C. | Clear for about 4 days at 40° C./75% RH and about 6-8 days 25° C./60% RH Clear solution for about 1 month, 15 days when stored at 2-8° C. |
| Chemical stability | Close to 2% impurity generated at 25° C./60% RH just after 16 days. | Just 2.62% impurity even after one month at 25° C./60% RH |

It was surprising to note that magnesium chloride has stabilizing effect on the physical and chemical stability of daptomycin in non-aqueous solutions in presence of cysteine.

Example 5: Solvent Effect on Stability of Daptomycin in Formulation Containing Cysteine and Magnesium Chloride

TABLE 10

Formulation composition for 9 and 10

| Ingredients | 9 | 10 |
|---|---|---|
| Daptomycin | 250 mg | 250 mg |
| Propylene Glycol | 5 mL | 3 ml |
| Glycerol | — | 2 mL |
| Magnesium Chloride | 30 mg | 30 mg |
| Cysteine | 50 mg | 50 mg |

Process: Daptomycin and other excipients were taken in solvent or mixture of solvents and sonicated until clear solutions were formed.

TABLE 11

Stability of data of Formulation 9 and 10.

| Stability time period | Temp/ humidity | Formulation no 9 Peak purity % | 9 Impurity % | 10 Peak purity % | 10 Impurity % |
|---|---|---|---|---|---|
| Initial | | 98.95 | 1.05 | 98.96 | 1.04 |
| 10 days | 40° C./75% RH | Not done | Not done | 97.41 | 2.59 |
| 10 days | 25° C./60% RH | 98.28 | 1.72 | 98.70 | 1.30 |
| 1 month, 15 days | 25° C./60% RH | 96.47 | 8.46 | 96.47 | 3.53 |
| 2 months | 2-8° C. | 99.40 | 0.60 | 99.26 | 0.74 |
| Clarity | | Formulation turned turbid after 8 days at 40° C./75% RH and after 10 days at 25° C./60% RH. Slightly turbid after 2 months at 2-8° C. | | Formulation turned turbid after 10 days at 40° C./75% RH and after 15 days at 25° C./60% RH. Clear after 2 months at 2-8° C. Turbid after 6 months at 2-8° C. | |

Observations: Formulation 10 was found to be more stable physically and chemically compared to Form-9 and hence it can be inferred that inclusion of glycerol has a positive effect on the stability of daptomycin in solution.

Example 6: Formulations with Varying Concentration of Cysteine and Fixed Amount of Magnesium Chloride

TABLE 12

Composition of Form 11-15

| Ingredients | 11 | 12 | 13 | 14 | 15 |
|---|---|---|---|---|---|
| Daptomycin. | 250 mg | 250 mg | 250 mg | 250 mg | 250 mg |
| Cysteine | 3 mg | 4 mg | 5 mg | 7.5 mg | 10 mg |
| Magnesium Chloride | 30 mg | 30 mg | 30 mg | 30 mg | 30 mg |
| Glycerol | 2 mL | 2 mL | 2 mL | 2 mL | 2 mL |
| Propylene Glycol | 3 mL | 3 mL | 3 mL | 3 mL | 3 mL |

TABLE 13a

Stability data of Form. 11-15

| Stability condition | 11 Purity (%) | 11 Impurity (%) | 12 Purity (%) | 12 Impurity (%) | 13 Purity (%) | 13 Impurity (%) | 14 Purity (%) | 14 Impurity (%) | 15 Purity (%) | 15 Impurity (%) |
|---|---|---|---|---|---|---|---|---|---|---|
| 40° C./75% RH 3 days | 97.21 | 2.79 | 97.09 | 2.91 | 97.09 | 2.91 | 97.06 | 2.94 | 97.58 | 2.38 |
| 40° C./75% RH 6 days | 91.34 | 8.66 | 89.17 | 10.83 | 93.59 | 6.43 | 93.90 | 6.10 | ND | ND |
| 25° C./60% RH 1 month | 93.90 | 6.10 | 91.40 | 8.60 | 94.38 | 5.61 | 94.79 | 5.21 | 95.65 | 4.35 |
| 25° C./60% RH 2 months | 88.29 | 11.71 | 84.82 | 15.08 | 89.59 | 10.41 | 91.58 | 8.43 | 90.98 | 9.08 |

TABLE 13a-continued

Stability data of Form. 11-15

| Stability condition | 11 Purity (%) | 11 Impurity (%) | 12 Purity (%) | 12 Impurity (%) | 13 Purity (%) | 13 Impurity (%) | 14 Purity (%) | 14 Impurity (%) | 15 Purity (%) | 15 Impurity (%) |
|---|---|---|---|---|---|---|---|---|---|---|
| 2-8° C. 2 months | | | Not done | | | | | | 98.75 | 1.25 |
| 2-8° C. 5.5 months | | | | | | | | | 98.26 | 1.24 |
| Clarity | All these formulations remained clear even after one month at 40° C./75% RH and 2 months at 25° C./60% RH. | | | | | | | | | |

Note: Impurities presented here represent increase compared to standard injections. The peak at RRT 1.12 (Anhydrodaptomycin) is major impurity that increases over the time. The same impurity is also present in standard injections to the extent of 0.6 to 0.8%.

TABLE 13b

Long term stability data of Form-11, 12, 13 and 15 (One year at 2-8° C.), stored in glass vial sealed using aluminum crimp cap with Teflon septum.

| Parameter | Form-11 | Form-12 | Form-13 | Form-15 |
|---|---|---|---|---|
| Assay after 1 year at 2-8° C. | 93.08% | 93.58% | 94.09% | 95.37% |
| % Impurity anhydrodaptomycin | 2.76% | 2.69% | 2.83% | 2.52% |

**-Physical stability of formulations also depends on primary packing, Form-15 packed in screw cap glass vial opened couple of times has turned turbid after 7-8 months stored at 2-8° C., same formulation packed in glass vial sealed aluminum crimp cap with Teflon septum remained clear after one year at 2-8° C.

As can be seen from the data, the formulations demonstrated less than 5% anhydrous daptomycin impurity after 1 year under refrigerated conditions.

TABLE 14

Composition for Form 16-19

| Ingredients | 16 | 17 | 18 | 19 |
|---|---|---|---|---|
| Daptomycin | 250 mg | 250 mg | 250 mg | 250 mg |
| Cysteine | 15 mg | 20 mg | 25 mg | 37.5 mg |
| Magnesium Chloride | 30 mg | 30 mg | 30 mg | 30 mg |
| Glycerol | 2 mL | 2 mL | 2 mL | 2 mL |
| Propylene Glycol | 3 mL | 3 mL | 3 mL | 3 mL |

TABLE 15

Stability data of Form 16-19

| Stability condition | 16 Purity (%) | 16 Impurity (%) | 17 Purity (%) | 17 Impurity (%) | 18 Purity (%) | 18 Impurity (%) | 19 Purity (%) | 19 Impurity (%) |
|---|---|---|---|---|---|---|---|---|
| 40 C./75% RH 3 days | 97.75 | 2.22 | 97.91 | 2.05 | 98.19 | 1.8 | 98.61 | 1.36 |
| 40 C./75% RH 6 days | ND | ND | ND | ND | ND | ND | ND | ND |
| 25° C./60% RH 1 month | 95.82 | 4.18 | 96.38 | 3.62 | 97.18 | 2.82 | 97.93 | 2.07 |
| 25° C./60% RH 2 months | 91.07 | 8.92 | 93.58 | 6.42 | 96.50 | 3.49 | 97.49 | 2.51 |
| 2-8° C. for 2 months | 98.67 | 1.33 | 99.44 | 0.56 | 99.20 | 0.80 | 98.90 | 1.10 |
| 2-8° C. for 5 months, 10 days | 98.82 | 1.18 | 98.86 | 1.14 | 98.11 | 0.89 | 99.09 | 0.91 |
| Clarity | All these formulations remained clear for about 10 days at 40° C./75% RH and about 20 days at 25° C./60% RH. All formulations were clear at 2-8° C. after 2 months. | | | | | | | |

Note: The impurity in standard injection ranges from 0.70 to 0.90%. Also, it appears that impurity peak at RRT 1.12 seems to be reversible.

Observations: The cysteine concentration has positive effect on the chemical stability of daptomycin in solution. Purity of formulation increases as the concentration of cysteine in the formulation increases. On the other hand, the physical stability of the formulation is impacted by an increase in the concentration of cysteine. It can be observed from Form 11-15 that, clarity of solutions was persevered for more than a month at both 25° C./60% RH and 40° C./75% RH when cysteine concentration was ≤2 mg/mL. Turbidity develops slowly in the formulation containing >2 mg/mL of cysteine. Turbidity, however, is not indicative of long-term chemical stability.

Example 7: Formulations with Varying Concentration of Magnesium Chloride and Fixed Amount of Cysteine

TABLE 16

Composition for Form 20-22 with different amount of magnesium chloride

| Ingredients | Formulation number | | |
|---|---|---|---|
| | 20 | 21 | 22 |
| Daptomycin. | 250 mg | 250 mg | 250 mg |
| Cysteine | 25 mg | 25 mg | 25 mg |
| Magnesium Chloride | 35 mg | 40 mg | 45 mg |
| Glycerol | 2 mL | 2 mL | 2 mL |
| Propylene Glycol | 3 mL | 3 mL | 3 mL |

Each of these formulations was tested for stability in glass vials and using screw top caps.

TABLE 17

Stability of Formulations 20-22

| Stability condition | 20 | | 21 | | 22 | |
|---|---|---|---|---|---|---|
| | Purity (%) | Impurity (%) | Purity (%) | Impurity (%) | Purity (%) | Impurity (%) |
| 40° C./75% RH 3 days | 97.99 | 2..01 | 98.29 | 1.71 | 98.19 | 1.81 |
| 40° C./75% RH 10 days | 95.59 | 4.41 | 95.61 | 4.39 | 95.82 | 4.18 |
| 25° C./60% RH 12 days | 98.76 | 1.24 | 98.81 | 1.19 | 98.84 | 1.16 |
| 25° C./60% RH 1 month | 97.01 | 2.99 | 97.20 | 2.80 | 96.90 | 3.10 |
| 2-8° C. 2 months | 99.38 | 0.62 | 99.44 | 0.56 | 99.47 | 0.53 |
| 2-8° C. 6 months | 99.13 | 0.87 | 98.92 | 1.08 | 99.08 | 0.92 |
| Clarity at 40° C./75% RH | Clear for about 10 days | | Clear for about 12 days | | Clear for about 16 days | |
| Clarity at 25° C./60% RH | Clear for about 16 days | | Clear for about 22 days | | Clear for about one month | |

Observations: The stability results of Form 20-22 indicate that, physical stability of daptomycin solutions was greatly enhanced by increasing concentration of magnesium chloride. The chemical stability remained same irrespective of concentration of magnesium chloride. The accelerated conditions infer that the compositions would be stable for about 1 year or longer if stored in a sealed container using pharmaceutically acceptable sealed vial storage techniques such as those commonly used for aseptic storage of parenterals, i.e. glass vial systems including rubber stoppers and aluminum crimp enclosures.

Summary

This invention describes some surprising findings, following are listed

- Despite previous reports where, small molecular weight alcohols such as PEG, propylene glycol used to precipitate or crystallize daptomycin from in semi aqueous solutions, it was found that daptomycin is soluble in propylene glycol.
- In contrast to aqueous or semi aqueous solutions, daptomycin is relatively stable in non-aqueous solvents.
- Cysteine was found to be a great stabilizer for daptomycin in non-aqueous solvents, whereas other amino acids tested were not effective.
- Stabilizing effects of cysteine were not due to antioxidants as oxidation is not degradation pathway for daptomycin degradation in non-aqueous solvents.
- Main impurity generated in non-aqueous solvents is of aspartyl transpeptidation at asp-9 residue.
- Inclusion of cysteine in the formulation greatly reduces formation of aspartyl transpeptidation impurity. Mechanism of stabilization not exactly understood, but formation complex between daptomycin and cysteine cannot be ruled out, which in turn stabilizes daptomycin.
- Magnesium chloride has positive effect on both physical and chemical stability of daptomycin in presence of cysteine.
- Combination of propylene glycol and glycerol found to be better combination than propylene glycol alone, which by itself also provides a solvent suitable for some long term stability of daptomycin.
- Surprisingly, when we tested, Arginine, Glycine, Lysine and Cysteine, it was found that only lysine and cysteine were soluble in organic solvents. However, when these amino acids were incubated with daptomycin in propylene glycol, the stability was very poor with Glycine, Lysine and Arginine. Only cysteine was found to improve the stability of daptomycin. Even when Arginine was dissolved in propylene glycol with addition of citric acid, the stability of daptomycin did not improve.

Hence, our inventions comprising of cysteine and magnesium chloride are found to be surprising as the formulations were stable for at least 12 days at 40 C/75% RH with increase impurity being <7% and in some of embodiments was <3%. The selected compositions with cysteine and magnesium chloride were stable for 1 month at 25 C/60% RH with impurity <3.5%.

The invention claimed is:

1. A non-aqueous liquid daptomycin composition, comprising
   a. from about 25 to about 250 mg/ml of daptomycin;
   b. from about 1.0 to about 3 mg/ml cysteine;
   c. from about 3 to about 10 mg/ml magnesium chloride; and
   d. a solvent comprising from about 50 to about 90%/vol propylene glycol and from about 10 to about 40%/vol glycerol.

2. The composition according to claim 1, wherein the daptomycin concentration is about 50 mg/ml or 150 mg/ml.

3. The composition according to claim 1, wherein the amount of propylene glycol is about 60%/vol.

4. The composition according to claim 1, wherein the amount of glycerol is about 40%/vol.

5. The composition according to claim 1, wherein the magnesium chloride concentration is about 6 mg/ml.

6. The composition according to claim 1, wherein the cysteine concentration is about 2 mg/ml.

7. The composition according to claim 1, wherein the solvent contains about 60%/vol propylene glycol and about 40%/vol glycerol.

8. The composition according to claim 7, wherein the concentration of daptomycin is about 50 mg/ml; the concentration of magnesium chloride is about 4 mg/ml and the concentration of cysteine is about 2 mg/ml.

9. The composition according to claim 7, wherein the concentration of daptomycin is about 150 mg/ml; the concentration of magnesium chloride is about 6 mg/ml and the concentration of cysteine is about 2 mg/ml.

10. The composition according to claim 1, wherein said composition maintains substantially optical clarity after 1 month at 25° C./60% relative humidity with no precipitation or particulate matter by visual observation.

11. The composition according to claim 1, wherein said composition has less than about 5% anhydrodaptomycin after 1 month at room temperature or 12 months at refrigerated temperatures.

12. The composition according to claim 1, wherein said composition has a peak purity of at least about 95% after 1 month at room temperature or 12 months at refrigerated temperatures.

13. The composition according to claim 1, further comprising an auxiliary solvent selected from the group consisting of ethanol, PEG 200, PEG 300, PEG 400 and mixtures thereof.

14. A non-aqueous liquid daptomycin composition, consisting essentially of 50-150 mg/ml of daptomycin, 1-3 mg/ml cysteine, 3-5 mg/ml magnesium chloride; 50-90%/vol propylene glycol and 10-40%/vol glycerol.

* * * * *